United States Patent
Netherly

[19]

[11] Patent Number: 5,947,961
[45] Date of Patent: Sep. 7, 1999

[54] BIOMEDICAL ELECTRODE HAVING SKIN-EQUILIBRATING ADHESIVE AT ITS PERIMETER AND METHOD FOR USING SAME

[75] Inventor: Samuel G. Netherly, Afton, Minn.

[73] Assignee: Minnesota Mining and Manufacturing Company, St. Paul, Minn.

[21] Appl. No.: 08/644,798

[22] Filed: May 10, 1996

[51] Int. Cl.$^6$ .................................................. A61B 17/39
[52] U.S. Cl. .............................. 606/32; 606/35; 607/142; 607/149; 607/152
[58] Field of Search .................................. 128/640, 641, 128/643, 644; 606/32, 35; 607/149, 152, 153; 600/373–392

[56] References Cited

U.S. PATENT DOCUMENTS

| | | | |
|---|---|---|---|
| 4,352,359 | 10/1982 | Larimore et al. | 128/640 |
| 4,387,714 | 6/1983 | Geddes et al. | 128/303.13 |
| 4,524,087 | 6/1985 | Engel | 427/2 |
| 4,539,996 | 9/1985 | Engel | 128/640 |
| 4,554,924 | 11/1985 | Engel | 128/640 |
| 4,643,193 | 2/1987 | De Marzo | 128/640 |
| 4,715,382 | 12/1987 | Strand | 128/640 |
| 4,776,350 | 10/1988 | Grossman et al. | 128/799 |
| 4,799,480 | 1/1989 | Abraham et al. | 607/152 |
| 4,848,348 | 7/1989 | Craighead | 128/639 |
| 4,848,353 | 7/1989 | Engel | 128/640 |
| 4,893,626 | 1/1990 | Henley et al. | 607/152 |
| 4,955,381 | 9/1990 | Way et al. | 128/640 |
| 4,979,517 | 12/1990 | Grossman et al. | 128/798 |
| 5,012,810 | 5/1991 | Strand et al. | 128/640 |
| 5,133,356 | 7/1992 | Bryan et al. | 128/640 |
| 5,150,708 | 9/1992 | Brooks | 128/640 |
| 5,215,087 | 6/1993 | Anderson et al. | 128/640 |
| 5,225,473 | 7/1993 | Duan | 524/388 |
| 5,276,079 | 1/1994 | Duan et al. | 524/386 |
| 5,330,527 | 7/1994 | Montecalvo et al. | 607/149 |
| 5,338,490 | 8/1994 | Dietz et al. | 252/500 |
| 5,352,315 | 10/1994 | Carrier et al. | 156/267 |
| 5,362,420 | 11/1994 | Itoh et al. | 252/500 |
| 5,385,679 | 1/1995 | Uy et al. | 252/500 |
| 5,394,877 | 3/1995 | Orr et al. | 128/662.03 |

FOREIGN PATENT DOCUMENTS

| | | | |
|---|---|---|---|
| 0 051 935 A2 | 5/1982 | European Pat. Off. | A61F 13/02 |
| WO 94/12585 | 6/1994 | WIPO | C09J 171/00 |
| WO 94/26950 | 11/1994 | WIPO | C23C 14/20 |
| WO 95/20634 | 8/1995 | WIPO | C09J 7/02 |

OTHER PUBLICATIONS

Anderson, *Dielectrics*, Chapman & Hall, London, pp. 14–28, 39–48 (1967).

Kim et al., "Uniformity of Current Density Under Stimulating Electrodes" *Critical Reviews in Biomedical Engineering* vol. 17, Issue 6, pp. 585–619 (1990).

*Primary Examiner*—Danton D. DeMille
*Attorney, Agent, or Firm*—Gary L. Griswold; John H. Hornickel

[57] ABSTRACT

A biomedical electrode is disclosed, having a geometry of a perimeter of hydrophilic adhesive exceeding the perimeter of an area containing electrically conductive plate(s). The geometry unexpectedly causes a reduction in edge effect for dispersive electrodes and cardiac stimulation electrodes due the substantial equilibration of the conductive adhesive with epidermis of a patient the electrode contacts for a period of time sufficient to cause such substantial equilibration.

3 Claims, 7 Drawing Sheets

BIOMEDICAL ELECTRODE HAVING SKIN-EQUILIBRATING ADHESIVE AT ITS PERIMETER AND METHOD FOR USING SAME

COLOR PHOTOGRAPHS

The file of this patent contains at least one drawing executed in color. Copies of this patent with color drawings will be provided by the Patent and Trademark Office upon request and payment of the necessary fee.

TECHNICAL FIELD

The present invention relates generally to biomedical electrodes of the type that delivers to or receives currents from a body, such as dispersive electrodes used to return current from a patient's body in electrosurgery or cardiac stimulating electrodes used to deliver current to a patient's body.

BACKGROUND OF THE INVENTION

Biomedical electrodes are used in a variety of applications and are configured to operate according to the size, type, and direction of current flowing into or out of a body of a patient.

Dispersive electrodes are used in electrosurgery. In modem surgical practice there are many times when electrosurgery is more preferable than the use of the traditional scalpel. In electrosurgery, cutting is performed by an intense electrical current passing through a cutting electrode. The surgeon directs this current to exactly where cutting is required by wielding the cutting electrode, which because of its cylindrical shape and the way it is held in the hand is commonly called an "electrosurgical pencil". By activating controls which change the characteristics of the electrical current being sent to the pencil by an electrosurgical generator, the surgeon can use the pencil either to cut or to coagulate areas of bleeding. This makes electrosurgery particularly convenient when surgery requiring extra control of blood loss is being performed. Because of concerns to minimize the transmissions of blood-borne illnesses between health care patients and health care providers, in both directions, electrosurgery is becoming increasingly important.

In electrosurgery, as in all situations where electrical current is flowing, a complete circuit must be provided to and from the current source. In this case, the current that enters the body at the pencil must leave it in another place and return to the generator. It will readily be appreciated that when current enough to deliberately cut is brought to the body of a patient in one place, great care must be taken that unintentional damage is not also done to the patient at the location where that current is leaving the body. The task of collecting the return current safely is performed by a dispersive electrode.

A dispersive electrode performs this task by providing a large surface area through which the current can pass; the same current which was at cutting intensity when focused at the small surface area at the tip of the pencil is relatively harmless, with the goal of being painless to the patient, when spread out over the large surface area of the dispersive electrode.

Unfortunately, any geometry of the large surface area has an edge and perhaps distinct corners or junctions where "edge effects" caused by increased current density at those locations can have a maximum temperature rise during usage by the patient making such dispersive electrode or cardiac stimulating electrode most uncomfortable to the patient.

Use of dispersive biomedical electrodes must account for the size of the electrode relative to the location of edges where current density is highest and where discomfort sensed in adjoining tissue of the patient caused by such current density.

The same difficulties concerning edge effect also are present in cardiac stimulating electrodes, such as those used for defibrillation, external pacing, or cardioversion. For a patient already in some discomfort or ill health, pain sensed by the very medical device intended to treat the patient is disconcerting at best to the patient.

SUMMARY OF THE INVENTION

The existence of edge effect on dispersive electrodes and cardiac stimulating electrodes is a well known and documented phenomenon, and due, in part, to the fact that the current is not evenly distributed on resistive type dispersive or stimulating electrodes. Such electrodes must be quite large to work properly without causing undue heating of the patient's tissues during use.

This invention solves problems for such electrodes that can cause undue heating of the patient's tissues during use by utilizing a very hydrophilic adhesive placed over a greater skin area than the conductive element(s) of the electrode. Preferably, the hydrophilic adhesive is also ionically conductive.

The principal purpose of this hydrophilic adhesive extending beyond the perimeter of the conductive element(s) of the electrode is not to provide larger area of ionic conductivity for passage of electrical signals at the interface between the electrode and skin of the patient, although use of a hydrophilic, conductive adhesive can have that supplemental benefit.

Unexpectedly, the principal purpose of this hydrophilic adhesive extending beyond the perimeter of the conductive element(s) is to equilibrate the water content of the adhesive with the water content of the epidermis, principally by absorbing water from the skin's epidermis, and cause impedance of the epidermis to be raised so that the current passing between the skin-electrode interface is more evenly distributed in the tissues of the patient contacting the electrode.

In other words, the purpose of this invention is to design a dispersive electrode that alters the impedance characteristics of the patient's tissues to reduce edge effect, whether present because of electrosurgical current density leaving the patient's body or because of cardiac stimulating current density entering the patient's body.

The biomedical electrode of the present invention has perimeter defining an area of at least one conductive element and a field of hydrophilic adhesive having an area extending beyond the perimeter of each conductive element, wherein the adhesive is formulated from a composition that encourages the rapid, substantial equilibration with (e.g., absorption of water from) epidermal tissues of a patient contacting the adhesive.

Substantial equilibration does not mean that the water content in the adhesive equals the water content in the epidermis. Rather, at some point, the balance between water content in the adhesive and water content in the epidermis stabilizes.

One conductive element is common in cardiac stimulating electrodes and dispersive electrodes, although at least two conductive elements are preferred for dispersive electrodes.

The time to substantial equilibration can depend on several factors, among which are health of the patient, location on the body, ambient humidity, adhesive formulation, occlusivity of backing, presence of ionic species in the adhesive, and the like. The adhesive formulation can be sufficient to permit rapid, substantial equilibration of water content in the epidermis with water content in the hydrophilic adhesive beyond the perimeter of each conductive element. Presence of ionic species can either promote or reduce water transport to or from the epidermis. Natural movement of water toward substantial equilibration begins with contact of the adhesive with epidermis. Desirably, the duration of rapid, substantial equilibration can be as little as about 5 minutes. Preferably, the duration can be greater than about 10 minutes and less than about 35 minutes. Most preferably, the duration can be between about 20 and about 30 minutes. The duration of rapid substantial equilibration should be a minimal time while also being sufficient to carry out the purpose of the present invention.

In preferred embodiments, the biomedical electrode according to the invention has a body contact portion defining a perimeter of the hydrophilic adhesive which is greater than a perimeter of conductive element(s) of the electrode.

Preferably, the adhesive is a biocompatible, pressure sensitive adhesive, and most preferably, an ionically conductive, biocompatible, pressure sensitive adhesive.

In some preferred embodiments, there is an optional field of lossy dielectric material between the conductor plate and a surface of the electrode that can contact a body of a patient. Such an optional layer helps to reduce the amount of maximum temperature rise caused by the electrosurgical current.

Embodiments of the invention are described using the following drawings.

BRIEF DESCRIPTION OF THE DRAWING

The reference numerals refer to like parts in the several views, wherein.

EMBODIMENTS OF THE INVENTION

Figure 1:
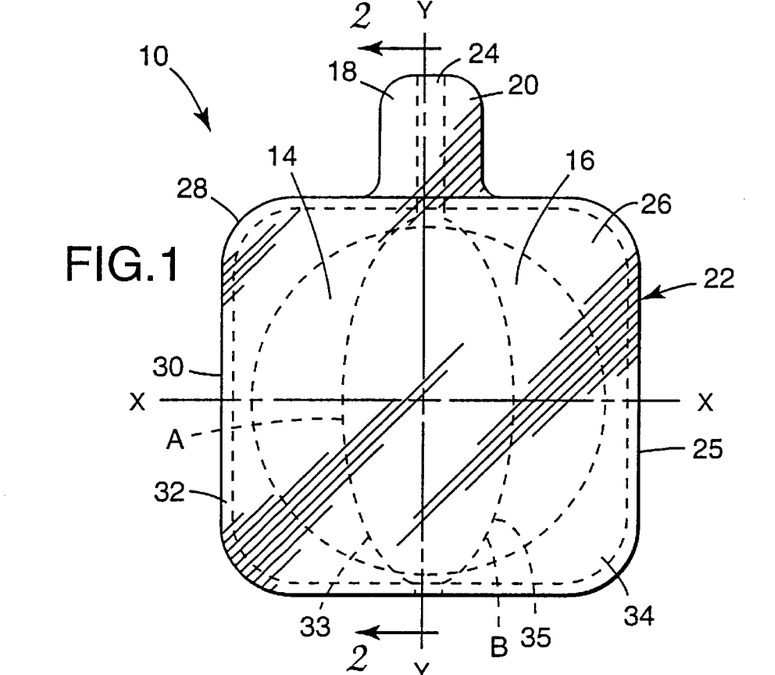
FIG. 1 is a bottom perspective view according to one presently preferred embodiment of the dispersive electrode of the present invention.

FIG. 1 shows a bottom perspective view of the dispersive electrode 10. The upper surface of the electrode 10, which is on the far side in this bottom view, can be a flexible and conformable electrically non-conductive backing 12. At least one conductor plate is needed for electrical contact with the body of a patient. In this embodiment, two conductor plates 14 and 16 are present along a longitudinal axis Y—Y matching Section line 2—2, adjacent to, and can be adhered to, the electrically non-conductive backipg 12. Two separate conductor plates are preferred because of their usefulness with contact quality monitoring ("CQM") circuitry because the impedance between the conductor plates 14 and 16 is measured by the above mentioned CQM circuits.

Each of the two conductor plates 14 and 16 has an extended tab 18 and 20, respectively, extending away from the body contact portion 22 of the electrode 10 for attachment of a cable assembly which connects the electrode 10 to an electrosurgical generator (not shown). When only one conductor plate is present on backing 12, there is only one extended tab. In order to provide more support for the conductor plates 14 and 16, and especially for their respective tabs 18 and 20, a non-conductive support layer 24 can be laminated to the conductor plates.

The region adjacent the exterior edge 25 of the body contact portion 22 of the electrode 10 can optionally be covered with a layer 26 of a lossy dielectric material. In the embodiment of FIG. 1, the width of the layer 26 of a lossy dielectric material is widest at the corners 28, and narrowest along the edge 30 midway between the corners. As presently understood, this arrangement of the layer 26 serves best to reduce edge effect at the corners 28 of the dispersive electrode. Further explanation of the use of a lossy dielectric material can be found in copending, coassigned U.S. patent application Ser. No. 08/628,182 (Netherly et al.), the disclosure of which is incorporated by reference herein.

Preferably, the entire body contact portion 22 of electrode 10 is covered with a field 32 of hydrophilic, ionically conductive, pressure sensitive adhesive for simplicity of manufacturing. Many compositions suitable for use for the field 32 of conductive adhesive are transparent, or at least translucent, and have been depicted that way in FIG. 1 for convenience in providing an explanatory drawing. The field 32 of adhesive serves the purpose of adhering the electrode 10 to the body of the patient. When the field 32 is adhesive that is ionically conductive, as it should be for those portions of field 32 contacting plates 14 and 16, the field also has the purpose of transferring the electrosurgical current between the body of the patient and the electrode for electrosurgical currents and between the electrode and the body for CQM monitoring.

Each of conductor plates 14 and 16 has an interior edge, 33 and 35 respectively, along the longitudinal axis Y—Y as seen in FIG. 1. Each of edges 33 and 35, or one of them, can be parallel, curvilinear or otherwise non-parallel to the opposing edge in a manner which creates a concave-inward indent relative to the longitudinal axis Y—Y. Preferably, both edges 33 and 35 have curvilinear geometries relative to the longitudinal axis, resulting in a double concave-inward indent symmetrical about the longitudinal axis. More preferably, the double concave-inward indent is also symmetrical about an axis orthogonal to the longitudinal axis, where the second axis is a latitudinal axis X—X substantially equidistant from edges of the body contact portion 22 orthogonal to the longitudinal axis. Most preferably, as seen in FIG. 1, at the point where longitudinal axis Y—Y and latitudinal axis X—X cross orthogonally, the non-conductive gap between edges 33 and 35 is maximal.

It will be seen that at point A which is away from the outside edge 25 of the body contact portion 22 of biomedical electrode 10, the minimum distance separating the conductive plates 14 and 16 is substantially greater than the minimum distance separating the conductive plates at a point B nearer the outside edge of the body contact portion.

Figure 2:
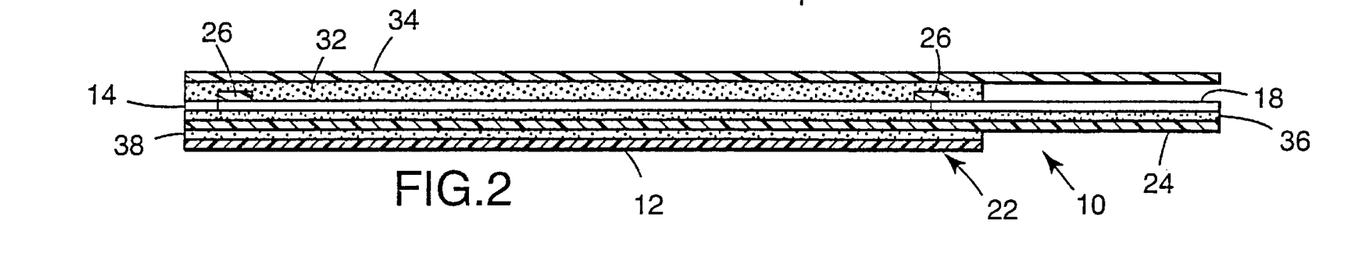
FIG. 2 is a cross-section view which is taken along section lines 2—2 in FIG. 1.

FIG. 2 shows a cross-section view of the electrode shown in FIG. 1, taken along section lines 2—2. In this view, a release liner 34 is shown adhered to the field 32 of hydrophilic adhesive. In those portions of electrode 10 where adhesive field 32 contacts one or more conductive plates 14 and 16, the adhesive field 32 is also ionically conductive. This release liner 34 protects the adhesive during shipping and handling and is removed just prior to use. In this view a layer of adhesive 36 is seen adhering the support layer 24 to conductor plate 14 and its extended tab 18. Another layer of adhesive 38 is provided for adhering the electrically non-conductive backing 12 to the other side of the support layer 24.

Electrically Non-conductive Backing

Electrically non-conductive backing 12 can be electrically insulative, and preferably is very conformable to the various contours of the mammalian body. Many materials can be used for this purpose, as will be apparent to those skilled in the art. In one presently preferred embodiment, a closed-cell foam is considered particularly suitable. One such material is commercially available as VOLARA brand foam from Voltek, Inc. of Massachusetts. The electrically non-conductive backing can have a thickness ranging from about 0.75 mm (0.03 inch) to about 1.5 mm (0.06 inch), and preferably 1.0 mm (0.04 inch).

Conductor Plates and Support Layer

The conductor plates 14 and 16 are conveniently made from metal, preferably in the form of a foil, a metal-containing or graphite-containing coated ink or paint, or a vapor coated metal, and most preferably, aluminum foil. If a support layer 24 is not being used, a thickness of about 0.08 mm (0.0003 inch) is considered preferred. If a support layer 24 is being used, the metal foil or vapor coated metal can be thinner because of the support provided by the support layer. A suitable support layer 24 can be made from polyethylene terephthalate (PET) film, conveniently approximately 0.05 mm (0.002 inch) thick. This allows the aluminum layer to range in thickness between about 0.0075 mm (0.0003 inch) to about 0.025 mm (0.001 inch) and preferably 0.012 mm (0.0005 inch) or allows vapor coated metal to have a minimum thickness of about 1000 Angstroms. An example of vapor coated metal on a substrate is found in PCT Publication No. WO 94/26950, the disclosure of which is incorporated by reference herein.

Hydrophilic Adhesive

Each of the hydrophilic adhesives useful in the present invention should be biocompatible with mammalian skin and can be formulated in both ionically conductive and non-conductive embodiments. The ionically conductive adhesives are useful in contact with both mammalian skin and conductor plates 14 and 16. The non-conductive adhesives can be used beyond the perimeter of the conductor plates 14 and 16.

Preferably, if expense of a single field 32 of hydrophilic, ionically conductive, biocompatible, pressure sensitive adhesive is not greater than the expense during manufacturing of applying two different types of adhesive to comprise field 32, then a single field is used even if ionic conductivity is not required to be present in the perimeter section of field 32 not contacting conductor plates 14 and 16.

Nonlimiting examples of hydrophilic adhesives useful in connection with the present invention include those compositions disclosed in U.S. Pat. No. 4,524,087 (Engel); U.S. Pat. No. 4,539,996 (Engel); U.S. Pat. No. 4,848,353 (Engel) and U.S. Pat. No. 5,133,356 (Bryan et al),; U.S. Pat. No. 5,225,473 (Duan); U.S. Pat. No. 5,276,079 (Duan et al); U.S. Pat. No. 5,338,490 (Dietz et al); U.S. Pat. No. 5,362,420 (Itoh et al), U.S. Pat. No. 5,385,679 (Uy et al); copending and coassigned applications PCT Publication Nos. WO 95/20634 and WO 94/12585; and PCT Patent Application Ser. Nos. US95/17079 (Docket No. 51537PCT6A); US95/16993 (Docket No. 51290PCT8A); and US95/16996 (Docket No. 48381PCT1A), the disclosures of which are incorporated by reference herein. Further nonlimiting examples of hydrophilic adhesives that do not have ionically conductive properties but would be useful for the perimeter section of field 32 include U.S. Pat. Nos. 4,871,812 and 5,407,717 (both Lucast et al.); U.S. Pat. No. 4,981,903 and Re 34,958 (both Garbe et al.); U.S. Pat. No. 5,009,224 (Cole); U.S. Pat. No. 5,232,838 (Nelson et al.); and U.S. Pat. No. 5,270,358 (Asmus); PCT Publication WO 95/27016; and adhesives commercially available from the Medical Specialties Department of 3M Health Care, 3M Company, St. Paul, Minn., the disclosures of all of which are incorporated herein by reference.

Release Liner

Release liner 34 can be any construction suitable for protecting the conductive adhesive 32 during shipping and handling while still releasing easily from the conductive adhesive at the time of use. One suitable liner is a 0.05 mm (0.002 inch) thick sheet of biaxially oriented polypropylene liner, commercially available as Daubert 164Z from Daubert Co. of Dixon, Ill.

Adhesive Layers

In some presently preferred embodiments, adhesive layers 36 and 38 may be used for holding other components of the electrode 10 together. Nonlimiting examples suitable adhesives 36 and 38 include acrylate ester adhesives, and more particularly acrylate ester copolymer adhesives. Such adhesives are generally described in U.S. Pat. Nos. 2,973,826; Re 24,906; Re 33,353; 3,389,827; 4,112,213; 4,310,509; 4,323,557; 4,732,808; 4,917,928; 4,917,929; and European Patent Publication 0 051 935, all incorporated herein by reference.

Optional Lossy Dielectric Layer

The layer 26 of lossy dielectric material has the performance parameters identified above in association with the ultimate performance of electrode 10 to minimize the maximum rise in temperature of tissue of a patient during electrosurgical procedures.

The lossy dielectric layer 26 can occupy an area of the body contact portion 22 ranging from about 5% to about 70% and preferably from about 40% to about 60%.

The lossy dielectric layer 26 can be made from a material and be applied in a non-uniform thickness to result in an electrical impedance gradient from the center of the body contact portion 22 to the exterior edge 25 ranging from about 30% to about 90% of the maximum impedance at exterior edge 25, and preferably from about 50% to about 70% of the maximum impedance at exterior edge of body contact portion 22.

The layer 26 can have a maximum impedance/area at the exterior edge 25 of the body contact portion 22 of the electrode 10 ranging from about 0.387 $\Omega/129$ cm$^2$ to about 20 $\Omega/129$ cm$^2$ and preferably ranging from about 1 $\Omega/129$ cm$^2$ to about 8 $\Omega/129$ cm$^2$, as determined by use of a Schlumberger 1260 spectrum impedance analyzer, operating at a frequency of 500 kHz and a constant voltage of 60 mV (RMS), and subjected to a nulling file to subtract out the effects of leadwires, connecting clips, and test fixture. A dispersive electrode of approximately 129 cm$^2$ (20 in$^2$) is the approximate size of most commercially available dispersive electrodes.

The layer 26 can have a resistance component per unit area (R/area) of the complex impedance Z of from about 0.4 $\Omega/129$ cm$^2$ to about 5 $\Omega/129$ cm$^2$ at exterior edge 25 on the dispersive electrode 10. Preferably, the layer 26 can have a resistance component per unit area ranging from about 0.5 $\Omega/129$ cm$^2$ to about 1.4 $\Omega/129$ cm$^2$. These values were determined as done for the maximum impedance per unit area.

The layer 26 can have a reactance component per unit area (X/area) of the complex impedance of from about −0.5 $\Omega/129$ cm$^2$ to about −16 $\Omega/129$ cm$^2$ at exterior edge 25 on the dispersive electrode 10. Preferably, the layer 26 can have a reactance component per unit area ranging from about −2 $\Omega/129$ cm$^2$ to about −10 $\Omega/129$ cm$^2$, using the same testing method as above for resistance per unit area and impedance per unit area.

The layer 26 can have a tan δ ranging from about 0.14 to about 1.7 at exterior edge 25 on the electrode 10, when measured at 500 kHz and a signal amplitude of 60 mV (RMS). Desirably, the tan 6 can range from about 0.2 to about 1.0 at exterior edge 25 on the electrode 10, when measured at 500 Hz and a signal amplitude of 60 mV (RMS). Preferably, the tan δ ranging from about 0.2 to about 0.7 at exterior edge 25 on the electrode 10, when measured at 500 Hz and a signal amplitude of 60 mV (RMS).

Layer 26 can be made from any lossy dielectric material that can be applied to body contact portion 22 and provide the performance parameters identified above for layer 26.

Layer 26 can be formed from an ink or paint on body contact portion 22 according to electrode manufacturing techniques known to those skilled in the art. It has been found particularly convenient to provide this material in the form of a paint, which can then be screen printed or sprayed in an appropriately shaped pattern onto the electrode 10 at the proper time during its fabrication. Oil-based enamels, commercially available as Cat. nos. 7776, 7790, 7730, 7727, and 7715 from Rust-oleum Corp. of Vernon Hills, Ill. are considered particularly suitable. Inks such as Summit UVII 300, UVII 800, and UVII 801 white inks, from Summit, Inc. of North Kansas City, Mo. can also be used. Additional information on the use of a lossy dielectric layer to reduce the heating caused by edge effect can be found in co-pending and co-assigned U.S. patent application Ser. No. 084 628, 182, the entire disclosure of which is hereby incorporated by reference.

Method of Making Electrodes

Electrode 10 can be made using conventional tab/pad style electrodes as described in U.S. Pat. No. 4,352,359 (Larimore); U.S. Pat. No. 4,524,087 (Engel), U.S. Pat. No. 4,539,996 (Engel); U.S. Pat. No. 4,554,924 (Engel); U.S. Pat. No. 4,848,348 (Carim); U.S. Pat. No. 4,848,353 (Engel), U.S. Pat. No. 5,012,810 (Strand et al.); U.S. Pat. No. 5,133,356 (Bryan et al.); U.S. Pat. No. 5,215,087 (Anderson et al.); and U.S. Pat. No. 5,296,079 (Duan et al.), the disclosures of which are incorporated by reference herein. Generally, multiple layered electrode 10 can be assembled from rolls of starting materials for insulative electrically non-conductive backing 12, upon which is applied conductor plates 14 and 16, upon which is coated paints or inks to form lossy dielectric layer 26, upon which is coated or cured field 32 of hydrophilic, ionically conductive pressure sensitive adhesive. Alternatively, a sheet of lossy dielectric material of a desired geometrical shape can be laminated onto conductor plates 14 and 16.

Automated machinery can be employed to make electrode 10. One skilled in the art of making electrodes can select from a variety of machinery manufacturers and manufacturing techniques to minimize manufacturing expense and waste. Some types of machinery are disclosed in U.S. Pat. No. 4,715,382 (Strand); U.S. Pat. No. 5,133,356 (Bryan et al.); and copending, coassigned U.S. patent application Ser. No. 08/343,253 (Yasis et al.), the disclosures of which are incorporated by reference herein, and U.S. Pat. No. 5,352, 315 (Carrier et al.).

USEFULNESS OF THE INVENTION

The use of field 32 of adhesive beyond the areas of the conductor plates 14 and 16 unexpectedly reduces edge effects and reduces the rise in temperature in tissue contacting the electrode during use of the electrode either as a dispersive electrode or as a cardiac stimulating electrode.

Because electrodes of this invention utilize a very hydrophilic adhesive, preferably conductive, placed over a greater skin area than the conductive element itself of the dispersive electrode, this adhesive border can equilibrate its water content with the water content in the epidermis of the patient, principally by absorbing water from the epidermis of the patient, and cause the impedance in tissues of patient in the area of body contact to be raised so that the current is more evenly distributed in the tissues of the patient. Unexpectedly, this invention has conceived a biomedical electrode that alters the impedance characteristics of the patient's tissues to reduce edge effect when the biomedical electrode is in use.

Biomedical electrodes of the present invention can be electrically connected to electrosurgical generators or cardiac stimulation devices to provide dispersive electrode connection or cardiac stimulation electrode connection, respectively. Electrosurgical generators are commonly available and known to those skilled in the art, such as devices marketed by Birtcher Medical Systems, Inc. of Irvine, Calif.; Aspen Surgical Systems, Inc. of Utica, N.Y.; and Valleylab, Inc. of Boulder, Colo. Cardiac stimulation devices for cardioversion, external pacing, and defibrillation are commonly available and known to those skilled in the art, such as devices marketed by Hewlett-Packard Corporation of McMinnville, Oreg.; Zoll Medical Corporation of Newton, Mass.; and Physiocontrol Corporation of Redmond, Wash.

Embodiments of the invention are further described in the following examples.

EXAMPLE 1

Two electrodes were constructed according the following procedure. An electrode was constructed from a 129 cm$^2$ cm (20 square inches) of Aluminum foil having corners with a radius of 2.54 cm. A layer of conductive adhesive was prepared according to the following procedure. Into a 300 gallon kettle equipped with overhead stirrer and a cooling jacket was charged 562.8 pounds (255.5 kg) acrylic acid, 1.4 pounds (636 grams) 2,2-dimethoxy-2-phenyl acetophenone, 2.8 pounds (1273 grams) 4-(2-hydroxyethoxy)phenyl-(2-hydroxy-2-methylpropyl)ketone, 1.12 pounds (508 grams) methylene bis(acrylamide), 1251.6 pounds (568.2 kg) glycerin, 2.8 pounds (1273 grams) guar gum, and 459.6 pounds (208.7 kg) deionized water. To the well stirred solution was charged 499.8 pounds (226.9 kg) 50% aqueous NaOH portionwise maintaining the batch temperture below 38° C. The hydroxide line was rinsed into the kettle with an additional 18 pounds (8.2 kg) deionized water and stirred for 30 minutes to yield coater-ready precursor. The precursor was coated onto the foil side of a polyester/aluminum foil laminate at 23 mil (0.6 mm) thick, overlaminated with a siliconized polyester liner, and passed through a curing chamber consisting of banks of fluorescent "black" lights, exposing the material to an intensity of 1.9 mW/sqcm and a total dose of 315 mJ/sqcm. The layer of conductive adhesive so prepared was then placed over the whole square of the electrically conductive surface. Each electrode was placed on an anterior thigh of a human (one on the left thigh and one on the right thigh) and left there for 30 minutes.

Figure 3:
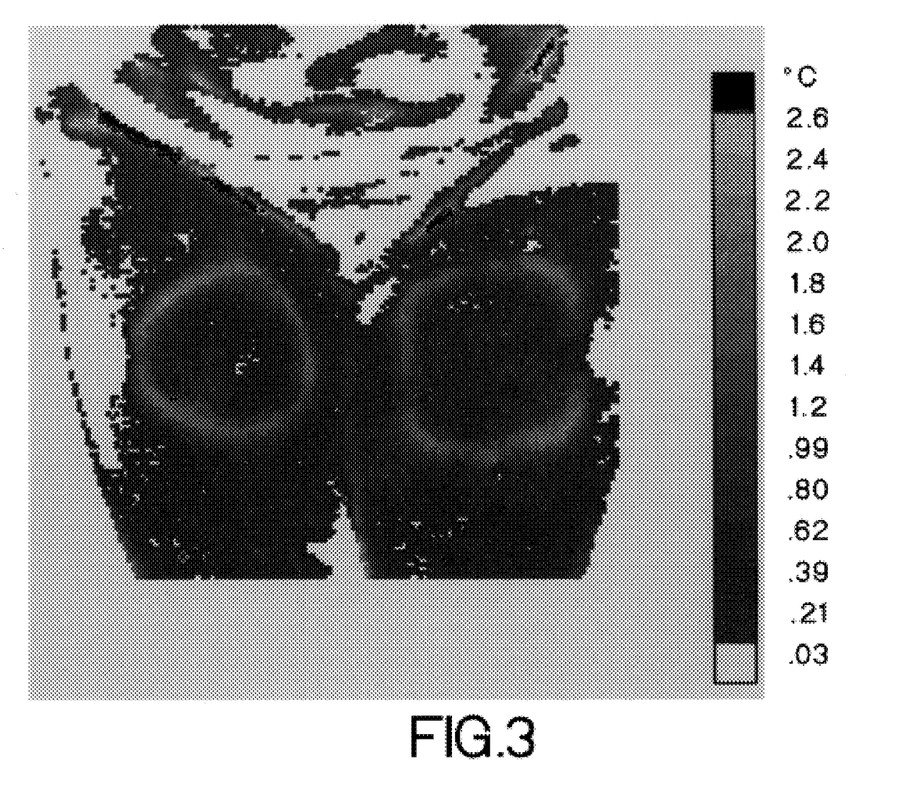
FIG. 3 is a thermogram of comparison of edge effect between an electrode of the present invention and a conventional electrode.

After 30 minutes, the electrode on the right thigh was peeled up at the corners and outer edges, so that the contact area was greatly reduced to about a minimum of 65 sq. cm. (from 20 square inches down to 10–12 square inches). Both electrodes were then energized according to the AAMI standard for thermography: 4.2.3.1, "Maximum Safe Temperature Rise" (1986) and the maximum tissue temperature rise on both anterior thighs were recorded using an Agema 470 Infra Red camera to measure temperature quantitatively. FIG. 3 shows the results, that the maximum tissue temperature rise of the right anterior thigh (left electrode in the thermogram) showed no trace of any additional temperature rise for the electrode originally equilibrated with patient's epidermis and then partially removed at the edges and corners as described above.

COMPARISON EXAMPLE 2

Figure 4:
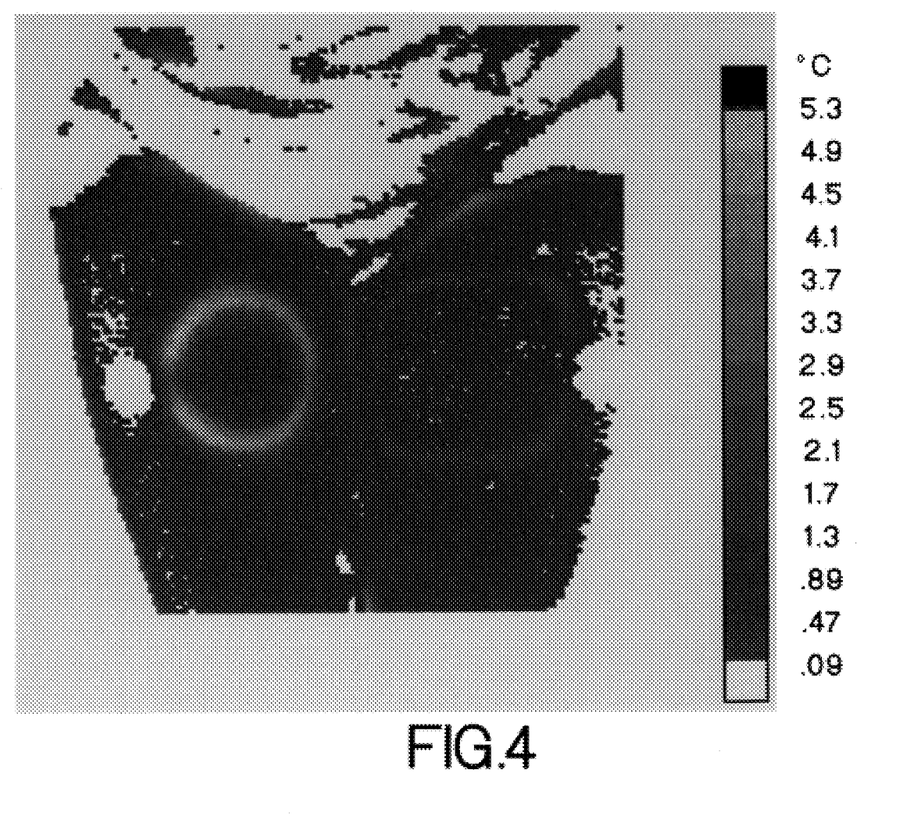
FIG. 4 is a thermogram of comparison of edge effect between an electrode of the present invention and a conventional electrode.

Electrodes were prepared in the same manner as in Example 1, except that one electrode was constructed in a circular shape having an area of 64.5 cm$^2$ (10 in$^2$). FIG. 4 shows the results of this comparison example where the circular electrode on the right anterior thigh (left electrode in the thermogram) had a very distinct and intense edge effect. This Comparison Example 2 verified that the unexpected effect of reduced edge effect found in Example 1 was not due solely to making an electrode with corners into an electrode with no corners by lifting the corners from contact with the epidermis.

COMPARISON EXAMPLE 3

Figure 5:
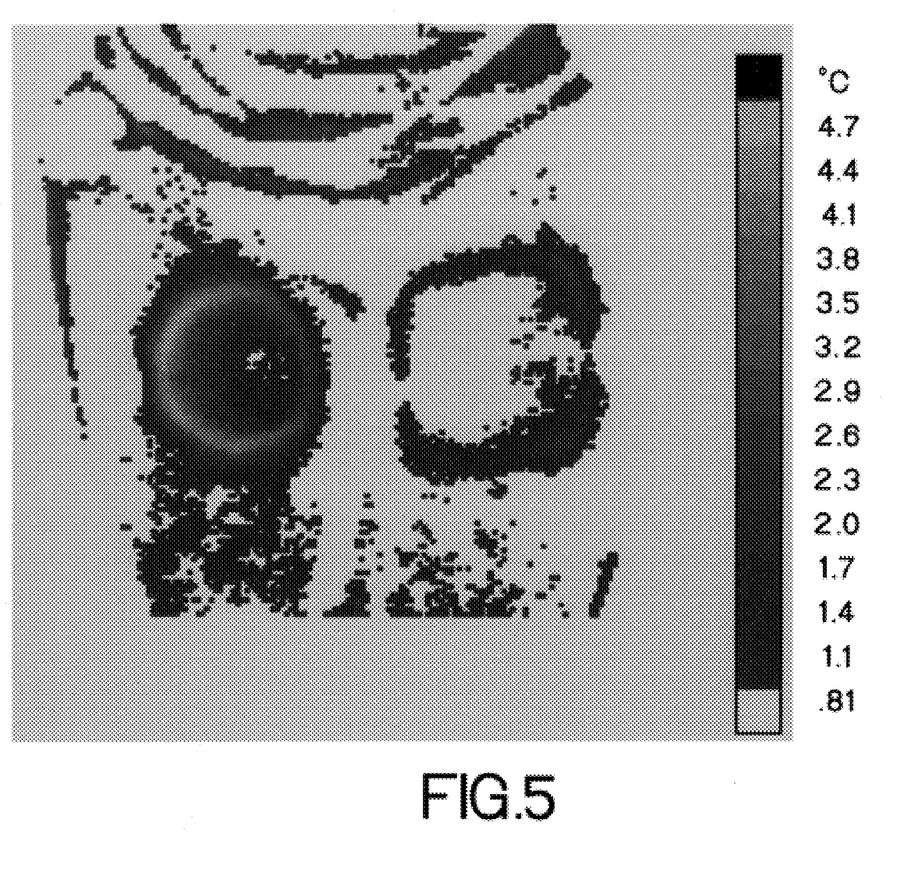
FIG. 5 is a thermogram of comparison of edge effect between an electrode of the present invention and a conventional electrode.

Electrodes were prepared in the same manner as in Example 1, except that one electrode was constructed to have radial slits cut around its periphery with a folding back on itself such that the contact area was 64.5 cm$^2$ (10 in$^2$). FIG. 5 shows the results of this comparison example where the circular electrode on the right anterior thigh (left electrode in the thermogram) had a very distinct and intense edge effect. This Comparison Example 3 verified that the unexpected effect of reduced edge effect found in Example 1 was not due solely to the way in which the EXAMPLE 1 right thigh electrode was folded back.

COMPARISON EXAMPLE 4

Figure 6:
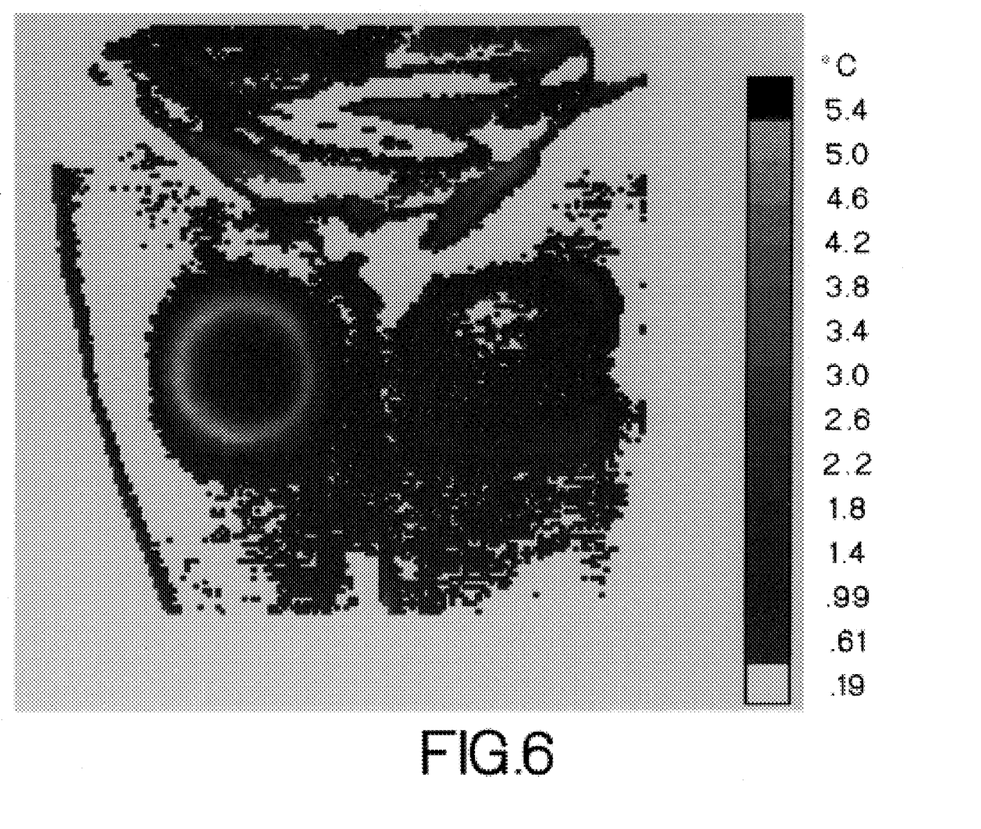
FIG. 6 is a thermogram of comparison of edge effect between an electrode of the present invention and a conventional electrode.

Electrodes were prepared in the same manner as in Example 1, except that one electrode was constructed to have a mask of foam with a 64.5 cm$^2$ (10 in$^2$) circle cut out of the middle and then placed over the conductive adhesive, so that 64.5 cm$^2$ (10 in$^2$) in the center of the electrode was in direct contact with the epidermis and another 64.5 cm$^2$ (10 in$^2$) around that was kept 1.14 mm (0.045 inches) (i.e., the thickness of the foam) away from the skin. FIG. 6 shows the results of this comparison example where the circular electrode on the right anterior thigh (left electrode in the thermogram) had a very distinct and intense edge effect. This Comparison Example 4 verified that the unexpected effect of reduced edge effect found in EXAMPLE 1 was not due solely to the way in which the EXAMPLE 1 right thigh electrode was distanced from the epidermis and causing some capacitive conduction from epidermis tissue to the electrode.

EXAMPLE 5

Figure 7:
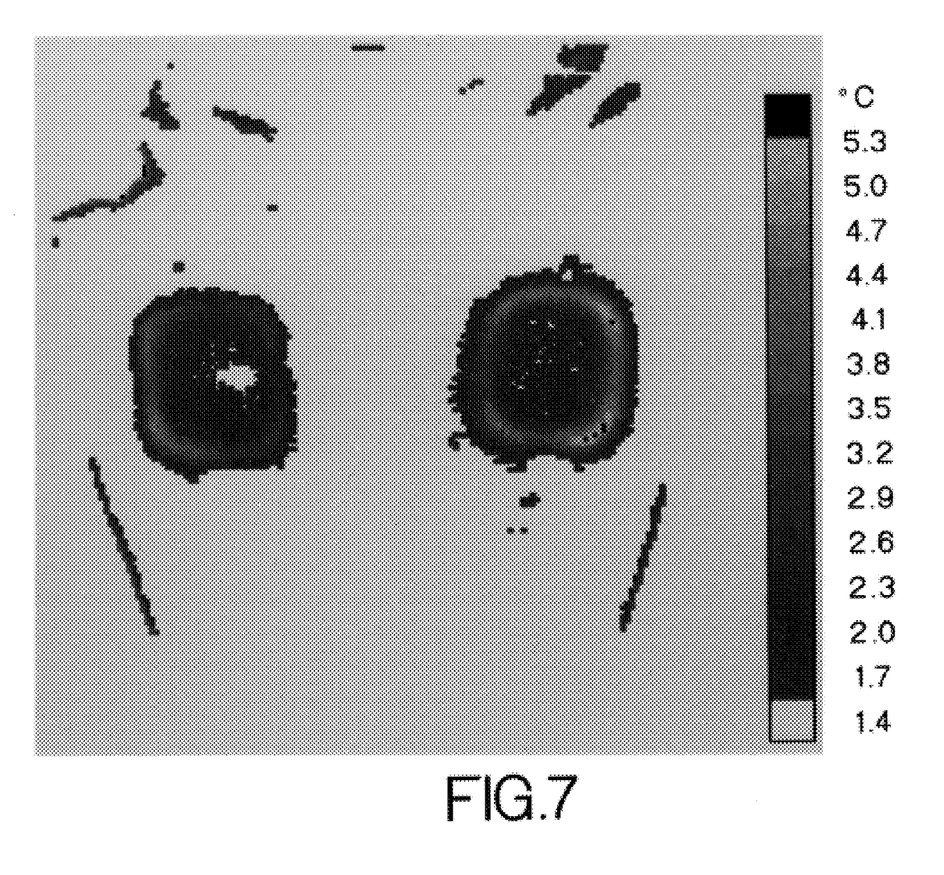
FIG. 7 is a thermogram of comparison of edge effect between an electrode of the present invsption and a conventional electrode.

A dispersive biomedical electrode commercially available as 3M brand Electrosurgical Patient Plate Catalog #7146 (64.5 cm$^2$ surface area) from 3M Company of St. Paul, Minn. was placed on the left anterior thigh of a patient. A dispersive biomedical electrode commercially available as 3M brand Electrosurgical Patient Plate Catalog #7149 (129 cm$^2$ surface area) from 3M Company of St. Paul, Minn. was placed on the right anterior thigh of a patient. After 30 minutes, the right thigh electrode was peeled back halfway to yield 64.5 cm$^2$ surface area and two very sharp (unradiused) corners. FIG. 7 shows the results of this example where the electrode peeled back, after substantial equilibration, on the right anterior thigh (left electrode in the thermogram) had a smaller maximum temperature rise than the unaltered left thigh electrode. This Example 5 verified that the unexpected effect of reduced edge effect found in EXAMPLE 1 was reproducible in commercially available electrodes.

EXAMPLE 6

Figure 8:
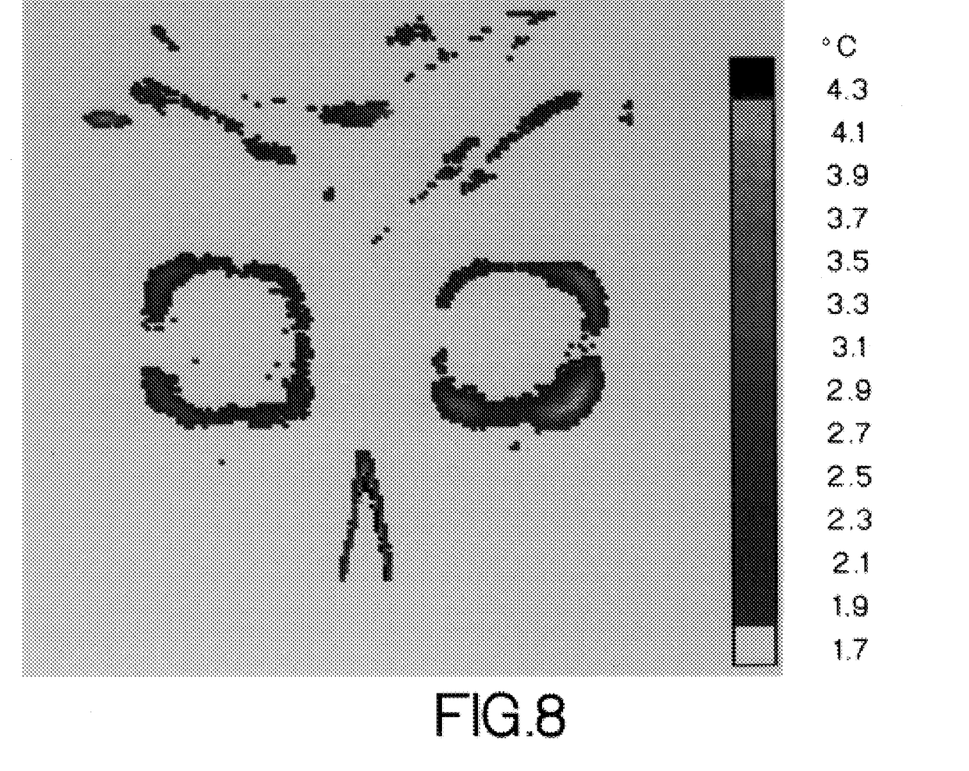
FIG. 8 is a thermogram of comparison of edge effect between an electrode of the present invention and a conventional electrode.

One electrode was prepared in the same manner as in Example 1, except that it was constructed to have a field of conductive adhesive having an area of a 129 cm$^2$ (20 in$^2$) and a 90.3 cm$^2$ (14 in$^2$) aluminum foil placed in the middle of the adhesive field. This right thigh electrode was substantially a resistive-type dispersive electrode with a conductive adhesive border around it. For the left thigh electrode, 14 square inch resistive-type dispersive electrode was constructed with the aluminum foil and the conductive adhesive being the same size and having the same perimeters. FIG. 8 shows the results of this example where the electrode having conductive adhesive extended beyond the perimeter of the aluminum foil on the right thigh (left electrode in the thermogram) had a smaller maximum temperature rise than the left thigh electrode having coterminus foil and adhesive perimeters. This Example 6 verified that the unexpected effect of reduced edge effect found in Example 1 was reproducible in simply constructed electrodes.

EXAMPLE 7

Electrodes were prepared in the same manner as in Example 1, except that one electrode was constructed to have a conductive plate of a size of 96.8 cm$^2$ (15 in$^2$) and a lossy dielectric coating on the border were tested with a larger (129 cm$^2$ (20 in$^2$)) layer of conductive adhesive and the other electrode was constructed to have the same size of conductive plate and lossy dielectric coating on the border but had conductive adhesive of the same perimeter as the conductive plate. While there was not a great difference in the resulting thermogram between these two electrodes, there was some maximum tissue temperature reduction with the lossy dielectric plate having a conductive adhesive exceeding the perimeter of the conductive plat, indicating that the reduction in edge effect due to a lossy dielectric coating can be coupled in series with the reduction in edge effect due to substantial equilibration of the electrode with the epidermis.

From this data of Examples 1–7, this invention finds the unexpected result of reduced edge effect: equilibrating contact of the hydrophilic adhesive of the electrode with the patient's tissue has the ability to alter the amount of edge effect seen in human tissue, after this adhesive has been in contact with the skin for about 30 minutes. During the testing in these Examples, some of the electrodes used were weighed before and after use, and there was a small but measurable weight gain after 30 minutes of equilibrating contact, indicating that water was transferred from the epidermis to the electrode. However, it is quite possible in some instances that substantial equilibration will occur in the opposite direction.

EXAMPLES 8–11

A dispersive biomedical electrode commercially available as 3M brand Electrosurgical Patient Plate Catalog #7149 from 3M Company of St. Paul, Minn. was cut in half to provide a 64.5 cmn$^2$ surface area with two very sharp (unradiused) corners and placed on the left anterior thigh of a patient. A second dispersive #7149 biomedical electrode was placed on the right anterior thigh of a patient. After 5 minutes, the right thigh electrode was peeled back halfway to yield 64.5 cm$^2$ surface area and two very sharp (unradiused) corners. The patient experienced some reduced discomfort on the right anterior thigh compared with the same electrode with the same area of contact on the left anterior thigh. The experiment was repeated three more times, only varying the time of duration of substantial equilibration for 10 minutes, 15 minutes, and 20 minutes, respectively. Increasing contact time from 5 to 15 minutes reduced the discomfort experienced by the patient. There was little discernible difference to the patient between the duration of 15 minutes and the duration of 20 minutes.

While not being limited to the embodiments disclosed above, the present invention also contemplates the possibility of constructing a plate with reduced edge effect by placing a smaller aluminum conductor over a larger area of a hydrophillic conductive adhesive. This construction is similar to the right thigh electrode shown in FIG. 8. To utilize this construction, one may have to increase the size of the conductive plate to reduce the edge effect as seen in FIG. 8.

Preferably, one could modify existing dispersive electrode and cardiac stimulating electrode constructions to replace the border fields of hydrophilic, biocompatible, but nonconductive skin adhesives with a hydrophilic conductive adhesive and gain the unexpected benefits of the present invention thereby reducing the edge effect could be reduced without an increase in the total area of the biomedical electrodeconductor and backing combined.

Various modifications and alterations of the present invention will be apparent to those skilled in the art without departing from the scope and spirit of this invention, and it should be understood that this invention is not limited to the illustrative embodiments set forth herein. The claims follow.

What is claimed is:

1. A method of using a biomedical electrode having at least one electrically conductive plate having a perimeter, and having a field of hydrophilic adhesive such that the perimeter of the hydrophilic adhesive exceeds the perimeter of the electrically conductive plate(s), comprising the steps of;

(a) placing the biomedical electrode on epidermis of a mammalian body; and (b) permitting water content in the hydrophilic adhesive of the electrode to substantially equilibrate with water content in the epidermis of the mammalian body to alter impedance characteristics of the epidermis.

2. The method of claim 1, wherein the permitting step results in absorption of water from the epidermis into the hydrophilic adhesive.

3. The method of claim 1, further comprising a step (c) of peeling back a portion of the biomedical electrode after the step (b) is completed.

* * * * *